United States Patent
Tanaka et al.

(10) Patent No.: US 6,740,060 B2
(45) Date of Patent: May 25, 2004

(54) GASKET FOR BYPASS TYPE PREFILLED SYRINGE

(75) Inventors: Nobuyoshi Tanaka, Hirakata (JP); Masahiko Kato, Amagasaki (JP)

(73) Assignee: Takeda Chemical Industries, Ltd., Osaka (JP)

( * ) Notice: Subject to any disclaimer, the term of this patent is extended or adjusted under 35 U.S.C. 154(b) by 174 days.

(21) Appl. No.: 10/092,536

(22) Filed: Mar. 8, 2002

(65) Prior Publication Data
US 2002/0138043 A1 Sep. 26, 2002

(30) Foreign Application Priority Data
Mar. 9, 2001 (JP) .......................... P2001-066620

(51) Int. Cl.[7] .............................. A61M 37/00
(52) U.S. Cl. ..................... 604/90; 604/89; 604/218; 604/236
(58) Field of Search .................. 604/187, 218, 604/82–92, 200–222, 236–238, 191, 199, 416, 231; 222/386, 195

(56) References Cited

U.S. PATENT DOCUMENTS

| | | | |
|---|---|---|---|
| 4,599,082 A | | 7/1986 | Grimard |
| 4,613,326 A | * | 9/1986 | Szwarc .................. 604/89 |
| 5,489,266 A | * | 2/1996 | Grimard ................ 604/89 |
| 5,685,846 A | * | 11/1997 | Michaels, Jr. .......... 604/90 |
| 5,743,890 A | * | 4/1998 | Hjertman et al. ....... 604/218 |
| 5,830,193 A | * | 11/1998 | Higashikawa .......... 604/191 |
| 5,851,200 A | * | 12/1998 | Higashikawa et al. ... 604/199 |
| 5,899,881 A | * | 5/1999 | Grimard et al. ........ 604/89 |
| 6,142,977 A | * | 11/2000 | Kolberg et al. ........ 604/218 |

* cited by examiner

Primary Examiner—Brian L. Casler
Assistant Examiner—Cris L. Rodriguez
(74) Attorney, Agent, or Firm—Wenderoth, Lind & Ponack, L.L.P.

(57) ABSTRACT

A bypass type prefilled syringe has a tubular body formed with a bypass for establishing communication between front and rear compartments for preliminarily storing medicament and pharmaceutical liquid, respectively. A gasket for dividing interior space of the tubular body into the front and rear compartments includes a plurality of circumferential ribs. A plurality of annular recesses are each formed between neighboring ones of the circumferential ribs. First and second axial slots are formed on the circumferential ribs so as to define a bent outflow path for the pharmaceutical liquid at the time of communication between the front and rear compartments via the bypass.

8 Claims, 8 Drawing Sheets

GASKET FOR BYPASS TYPE PREFILLED SYRINGE

BACKGROUND OF THE INVENTION

1. Field of the Invention

The present invention generally relates to a bypass type prefilled syringe in which a bypass for establishing communication between front and rear compartments for preliminarily storing two components, for example, powdery medicament and pharmaceutical liquid, respectively is formed on a tubular body, and more particularly to a gasket for dividing interior space of the tubular body of the bypass type prefilled syringe into the front and rear compartments.

2. Description of the Prior Art

Figure 6:
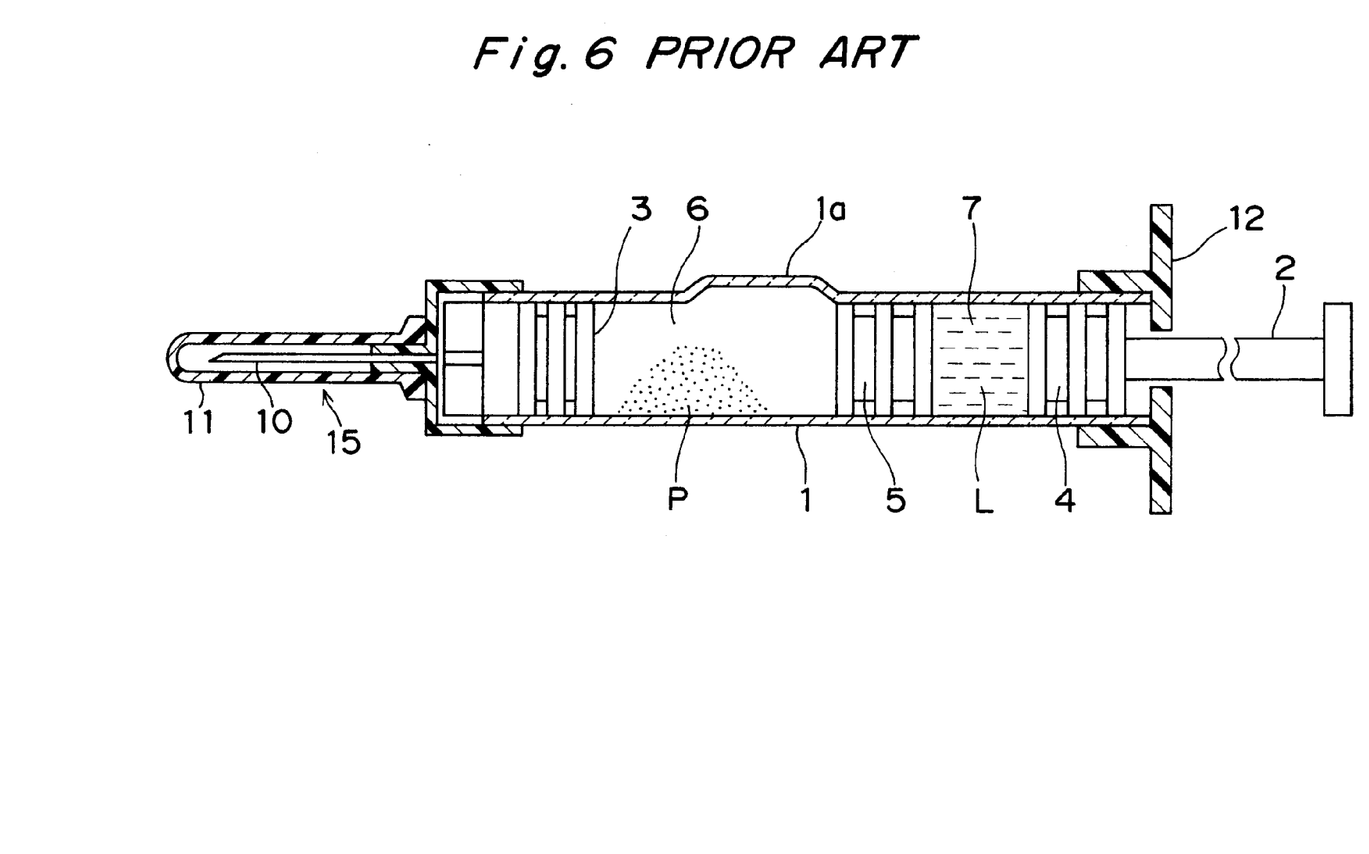
FIG. 6 is a schematic sectional view showing a sealing state between front and rear compartments of a prior art bypass type prefilled syringe.
Figure 7:
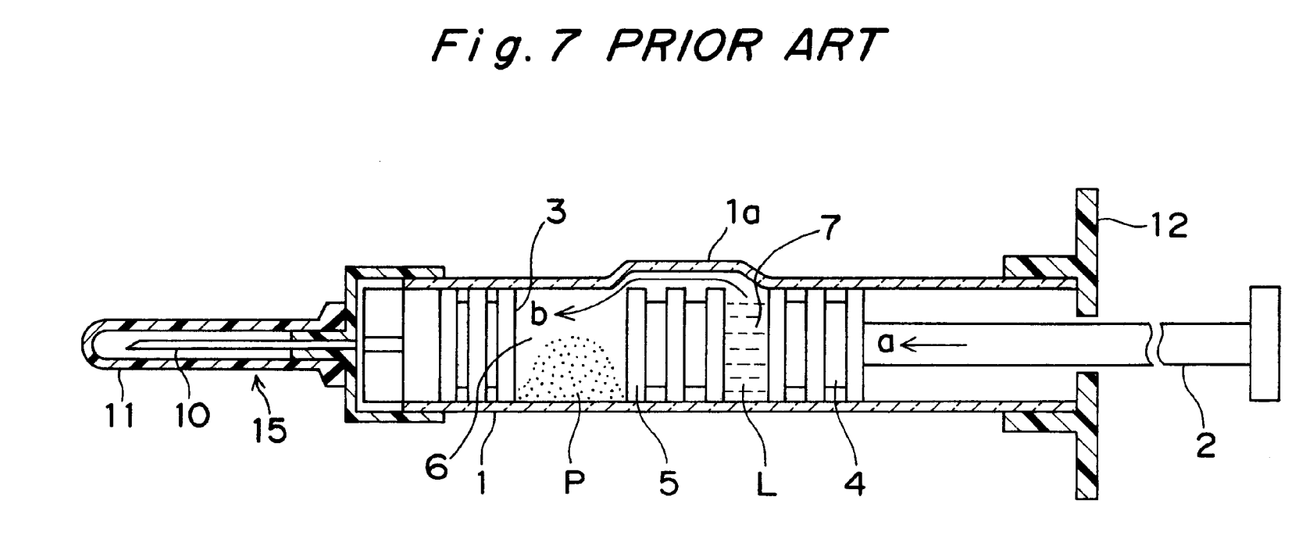
FIG. 7 is a schematic sectional view showing a communication state between the front and rear compartments of the prior art bypass type prefilled syringe of FIG. 6.

FIGS. 6 and 7 show a sealing state and a communication state between a front compartment 6 and a rear compartment 7 of an elongated hollow tubular body 1 of a conventional bypass type prefilled syringe, respectively. A front assembly 15 includes an injection needle 10 and a cap 11 for covering the injection needle 10 so as to protect the injection needle 10 and is mounted on an outer periphery of a front end portion of the tubular body 1. In FIG. 6, the conventional bypass type prefilled syringe includes a first sealing member 3 which is mounted in the front end portion of the tubular body 1, a second sealing member 4 which is attached to a front end of a plunger rod 2 and is disposed at a rear end portion of the tubular body 1 and a gasket 5 which is slidably inserted between the first and second sealing members 3 and 4 in the tubular body 1 and divides interior space of the tubular body 1 into the front and rear compartments 6 and 7. Powdery medicament P and pharmaceutical liquid L are preliminarily, respectively, stored in the front and rear compartments 6 and 7 so as to interpose the gasket 5 therebetween.

A bypass 1a is formed by bulging a peripheral wall of the front compartment 6 of the tubular body 1 radially outwardly. On the other hand, a finger grip 12 is mounted on an outer periphery of the rear end portion of the tubular body 1. By forwardly depressing the plunger rod 2 in the direction of the arrow a in FIG. 7 from the state of FIG. 6 to the state of FIG. 7, the gasket 5 is advanced by the second sealing member 4 by way of the pharmaceutical liquid L so as to be disposed between a front end portion and a rear end portion of the bypass 1a. At this time, a gap for directly linking the front and rear compartments 6 and 7 is defined between the gasket 5 and the bypass 1a, so that the front and rear compartments 6 and 7 are communicated with each other by the bypass 1a and thus, the pharmaceutical liquid L is introduced from the rear compartment 7 into the powdery medicament P in the front compartment 6 along a flow path indicated by the arrow b in FIG. 7. Then, when the powdery medicament P is sufficiently dissolved or dispersed in the pharmaceutical liquid L by shaking the tubular body 1, injection liquid is formed.

At the time of communication between the front and rear compartments 6 and 7 through the bypass 1a in this conventional bypass type prefilled syringe, the pharmaceutical liquid L is fed under pressure into the front compartment 6 in a state where the injection needle 10 is mounted on the tubular body 1. At this time, the gasket 5 is disposed between the front end portion and the rear end portion of the bypass 1a and the gap for directly linking the front and rear compartments 6 and 7 is defined between the gasket 5 and the bypass 1a as described above. Thus, in case a user forcibly depresses the plunger rod 2 from the state of FIG. 6 to the state of FIG. 7, a so-called squirt phenomenon in which the pharmaceutical liquid L spouts from the bypass 1a vigorously may happen, thereby resulting in such an inconvenience that the pharmaceutical liquid L impinges on the first sealing member 3 and then, leaks out of the injection needle 10.

Figure 8:
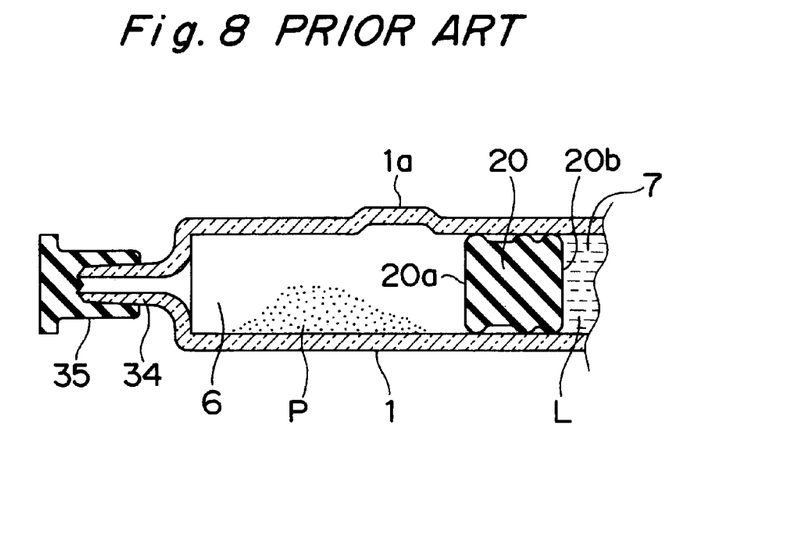
FIG. 8 is a schematic fragmentary sectional view showing a sealing state between front and rear compartments of a further prior art bypass type prefilled syringe.
Figure 9:
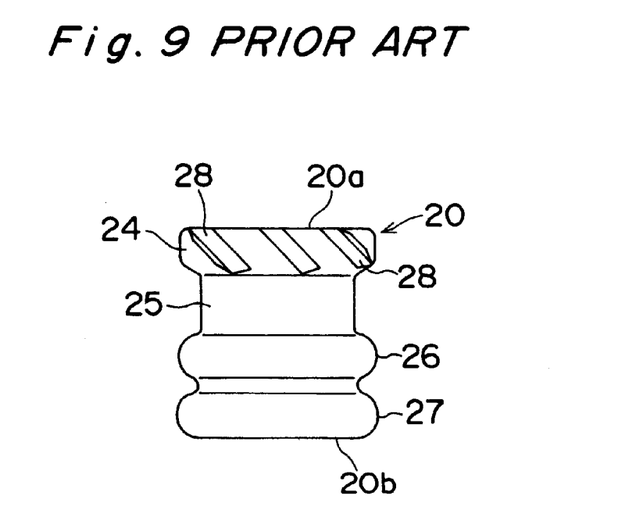
FIG. 9 is a front elevational view of a gasket employed in the further prior art bypass type prefilled syringe of FIG. 8.

Meanwhile, FIG. 8 shows a sealing state between the front and rear compartments 6 and 7 of the tubular body 1 of a known bypass type prefilled syringe disclosed in U.S. Pat. No. 4,599,082. In this known bypass type prefilled syringe, a gasket 20 is employed. As shown in FIG. 9, the gasket 20 has a front end face 20a and a rear end face 20b and includes ribs 24, 26 and 27. Meanwhile, an annular recess 25 is provided between the ribs 24 and 26 and a plurality of grooves 28 extending obliquely relative to an axis of the gasket 20 are formed on the rib 24 so as to open to the front end face 20a. In order to improve agitation and mixing of the pharmaceutical liquid L and the powdery medicament P at the time of communication between the front and rear compartments 6 and 7 via the bypass 1a, the pharmaceutical liquid L is introduced from the grooves 28 into the powdery medicament P obliquely relative to the axis of the gasket 20.

However, in contrast with the conventional construction shown in FIGS. 6 and 7 in which the injection needle 10 is mounted on the front end portion of the tubular body 1, this known bypass type prefilled syringe has a construction in which a distal end cap 35 is mounted on a distal end 34 of the tubular body 1. Thus, as described at column 8, lines 3 to 9 of the above mentioned U.S. Patent, mixing operation of the pharmaceutical liquid L and the powdery medicament P is performed by depressing a plunger rod in a state where the distal end 34 of the tubular body 1 is directed upwardly after the distal end cap 35 has been removed from the distal end 34 of the tubular body 1. Therefore, the gasket 20 merely serves to improve agitation and mixing of the pharmaceutical liquid L and the powdery medicament P and thus does not serve to prevent leakage of the pharmaceutical liquid L from an injection needle due to the squirt phenomenon.

SUMMARY OF THE INVENTION

Accordingly, an essential object of the present invention is to provide, with a view to eliminating the above mentioned drawbacks of prior art, a gasket for a bypass type prefilled syringe which prevents a squirt phenomenon of pharmaceutical liquid at the time of communication between front and rear compartments of a tubular body by way of a bypass such that powdery medicament can be sufficiently dissolved or dispersed in the pharmaceutical liquid.

In order to accomplish this object of the present invention, a gasket for a bypass type prefilled syringe having a tubular body formed with a bypass for establishing communication between front and rear compartments for preliminarily storing medicament and pharmaceutical liquid, respectively, according to the present invention divides interior space of the tubular body into the front and rear compartments and includes a plurality of circumferential ribs which include at least first, second and third circumferential ribs disposed sequentially further away from the front compartment. A plurality of annular recesses are each formed between neighboring ones of the circumferential ribs and include at least a first annular recess formed between the first and second circumferential ribs and a second annular recess formed between the second and third circumferential ribs. A first axial slot extends through the first circumferential rib and the first annular recess, while a second axial slot is formed at a circumferential position of the second circumferential rib deviating from the first axial slot so as to bring the first and second annular recesses into communication with each other. At the time of communication between the front and rear compartments via the bypass, a bent outflow path for delivering the pharmaceutical liquid into the front compartment in a state where the tubular body at a front end side of the bypass is closed by a front end portion of the gasket is sequentially formed by the second annular recess, the second axial slot, the first annular recess and the first axial slot.

BRIEF DESCRIPTION OF THE DRAWINGS

This object and features of the present invention will become apparent from the following description taken in conjunction with the preferred embodiment thereof with reference to the accompanying drawings in which.

Before the description of the present invention proceeds, it is to be noted that like parts are designated by like reference numerals throughout several views of the accompanying drawings.

DETAILED DESCRIPTION OF THE INVENTION

Figure 1:
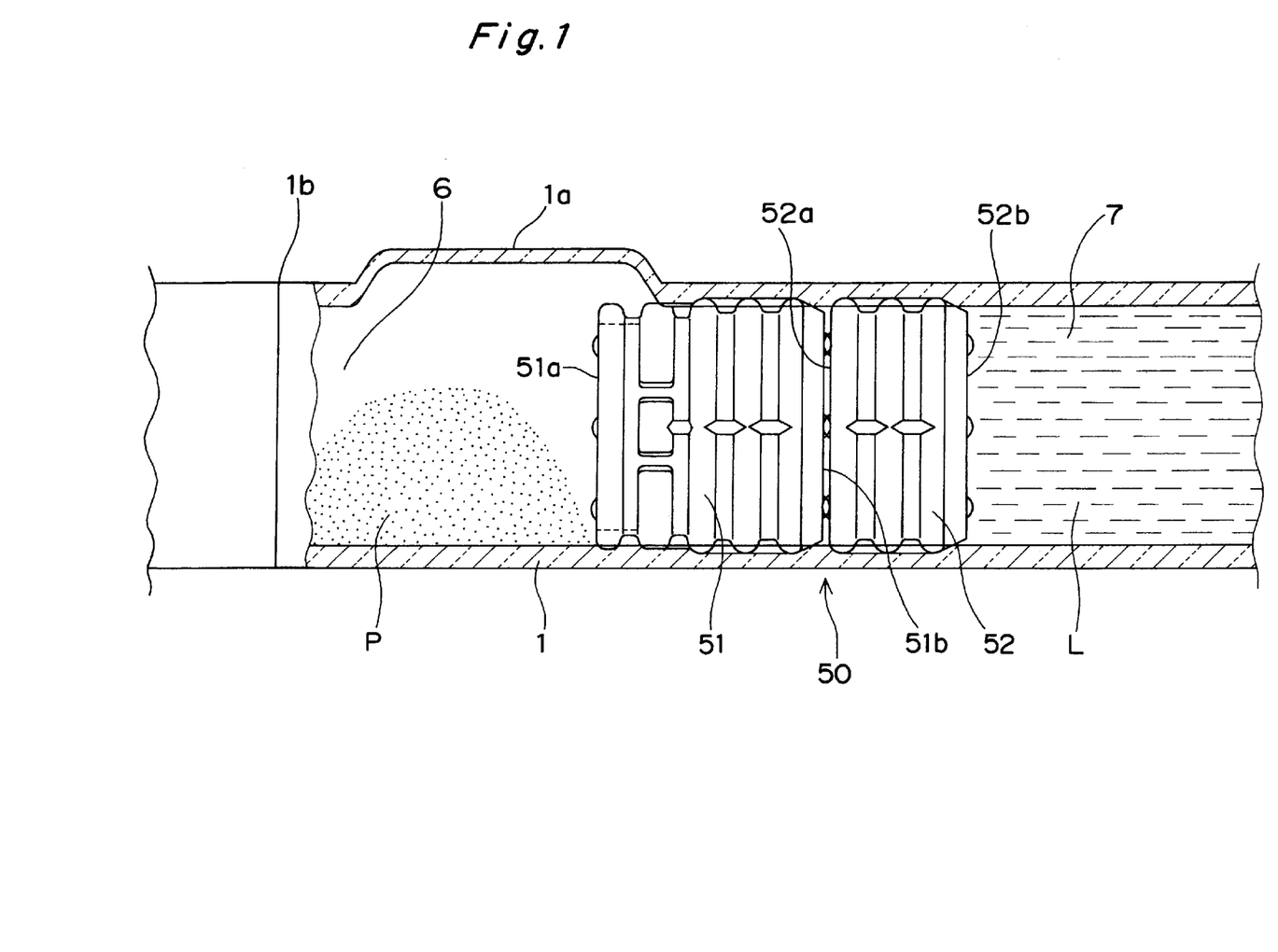
FIG. 1 is an enlarged schematic fragmentary sectional view showing a sealing state between front and rear compartments of a bypass type prefilled syringe including a gasket according to one embodiment of the present invention.
Figure 2:
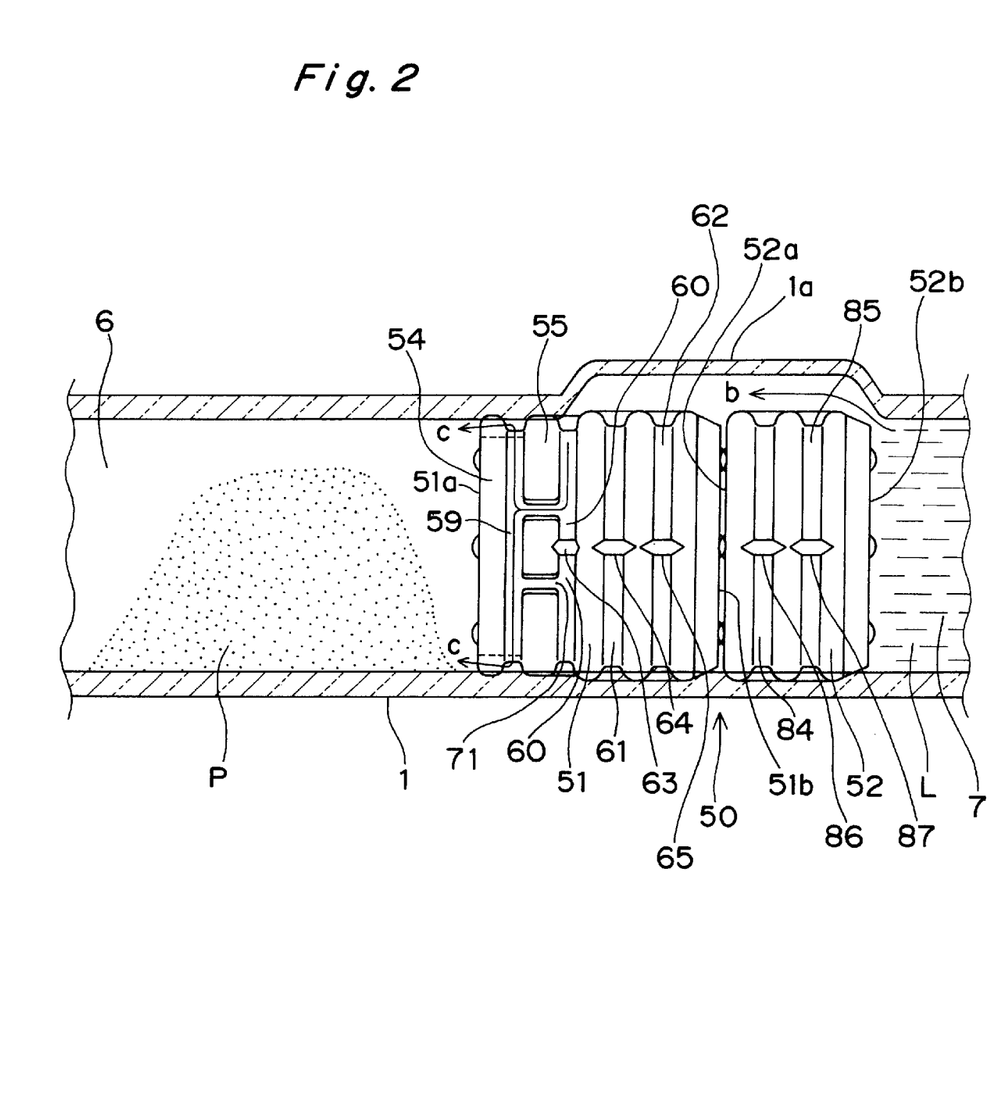
FIG. 2 is an enlarged schematic fragmentary sectional view showing a communication state between the front and rear compartments of the bypass type prefilled syringe of FIG. 1.

Hereinafter, one embodiment of the present invention is described with reference to the drawings. FIGS. 1 to 5 show a gasket 50 for a bypass type prefilled syringe according to the one embodiment of the present invention. In this bypass type prefilled syringe, powdery medicament P and pharmaceutical liquid L are, respectively, stored in a front compartment 6 and a rear compartment 7 of a tubular body 1 beforehand so as to interpose the gasket 50 therebetween, while a marked line 1b indicative of a position for temporarily stopping a front end of the gasket 50 at the time of communication between the front and rear compartments 6 and 7 via a bypass 1a is drawn forwardly of the bypass 1a as shown in FIG. 1. Since other constructions of the bypass type prefilled syringe are similar to those of a prior art bypass type prefilled syringe shown in FIGS. 6 and 7 in which a first sealing member 3 and a second sealing member 4 are provided and an injection needle 10 is mounted on a front end portion of the tubular body 1, the description is abbreviated for the sake of brevity. FIGS. 1 and 2 show a sealing state and a communication state between the front and rear compartments 6 and 7 of the tubular body 1, respectively.

As shown in FIGS. 1 and 2, the gasket 50 is constituted by a front gasket segment 51 and a rear gasket segment 52 which are disposed so as to abut on each other. However, the gasket 50 is not required to be constituted by the two components but may also be formed by the single front gasket segment 51 only. In this case, the bypass 1a should be set at a small dimension in conformity with the front gasket segment 51. The gasket 50 is made of elastomer such as synthetic rubber.

Figure 3A:
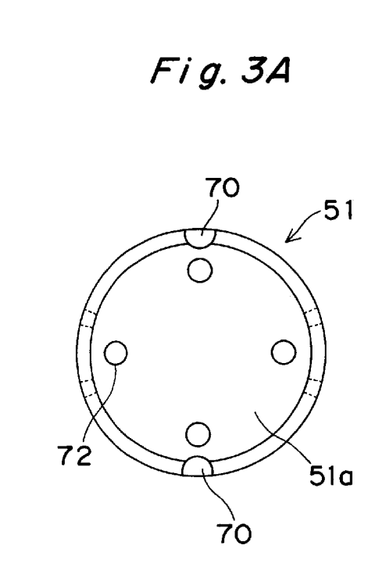
FIGS. 3A, 3B and 3C are, respectively, a left side elevational view, a front elevational view and a right side elevational view of a front gasket segment employed in the gasket of FIG. 1.
Figure 3B:
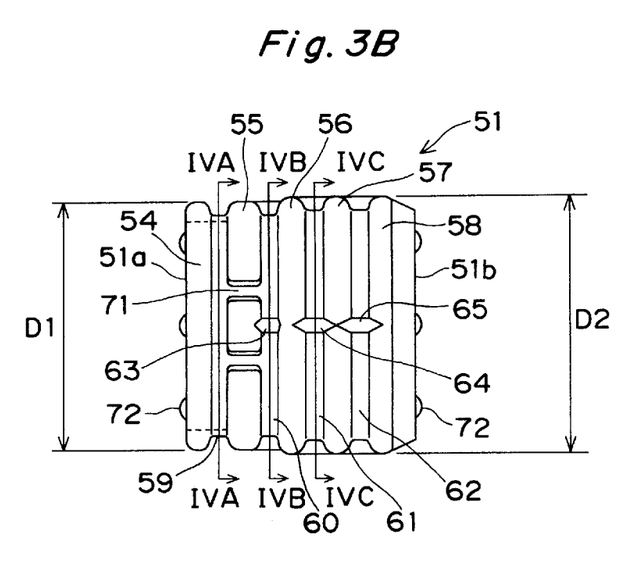
Figure 3C:
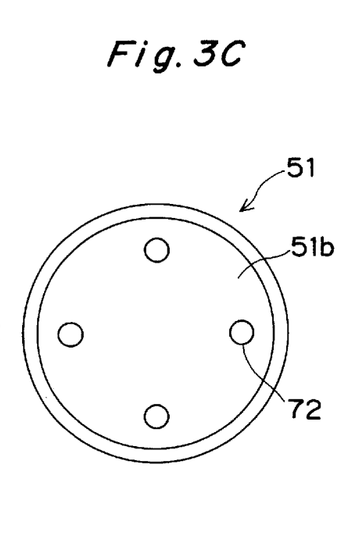
Figure 4A:
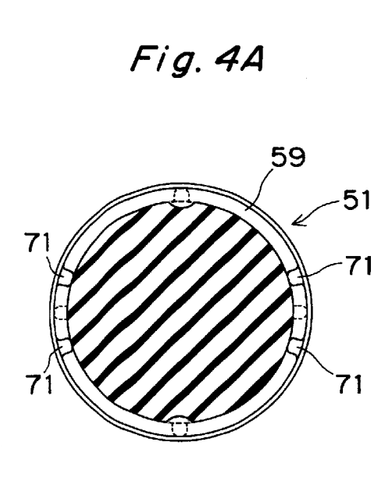
FIGS. 4A, 4B and 4C are sectional views taken along the lines IVA—IVA, IVB—IVB and IVC—IVC in FIG. 3B, respectively.
Figure 4B:
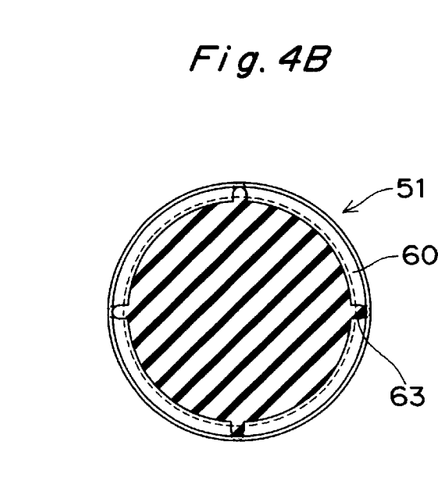
Figure 4C:
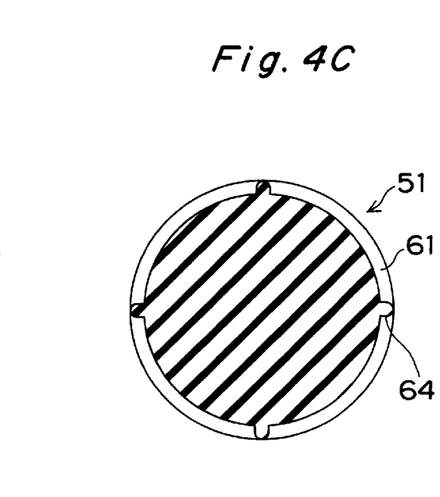

FIGS. 3A, 3B and 3C are a left side elevational view, a front elevational view and a right side elevational view of the front gasket segment 51, respectively, while FIGS. 4A, 4B and 4C are sectional views taken along the lines IVA—IVA, IVB—IVB and IVC—IVC in FIG. 3B, respectively. The front gasket segment 51 has a front end face 51a and a rear end face 51b each having four projections 72 and includes circumferential ribs 54, 55, 56, 57 and 58 arranged sequentially from the front end face 51a towards the rear end face 51b. The front gasket segment 51 further has an annular recess 59 formed between the circumferential ribs 54 and 55, an annular recess 60 formed between the circumferential ribs 55 and 56, an annular recess 61 formed between the circumferential ribs 56 and 57 and an annular recess 62 formed between the circumferential ribs 57 and 58.

Meanwhile, an axial rib 63 is provided at each of four circumferential positions of the annular recess 60. Likewise, an axial rib 64 is provided at each of four circumferential positions of the annular recess 61 and an axial rib 65 is provided at each of four circumferential positions of the annular recess 62. At the time of communication between the front and rear compartments 6 and 7, the axial ribs 63, 64 and 65 intercept the pharmaceutical liquid L flowing in the annular recesses 60, 61 and 62 so as to prevent the pharmaceutical liquid L from flowing through the annular recesses 60, 61 and 62, respectively such that the pharmaceutical liquid L in the annular recesses 60, 61 and 62 is carried forwardly.

Furthermore, two semicircular axial slots 70 are, respectively, formed at diametrically opposite ends of the circumferential rib 54 and extend through the circumferential rib 54 and the annular recess 59 so as to open to the front end face 51a. On the other hand, four axial slots 71 are, respectively, formed at circumferential positions of the circumferential rib 55 deviating from the axial slots 70 so as to bring the annular recesses 59 and 60 into communication with each other. As will been seen from FIGS. 3A and 4A, a cross-sectional area of a flow path of the axial slot 70 is set to be larger than that of the axial slot 71.

By setting an outside diameter D1 of the circumferential ribs 54 and 55 adjacent to the front end face 51a to be equal to or larger than an inside diameter of the tubular body 1 but smaller than an outside diameter D2 of the circumferential ribs 56, 57 and 58, the gasket 50 can be advanced smoothly while a sealing state between the tubular body 1 and the gasket 50 is being secured. Meanwhile, an outside diameter of the annular recesses 59 and 60 is also set to be smaller than that of the annular recesses 61 and 62.

Figure 5:
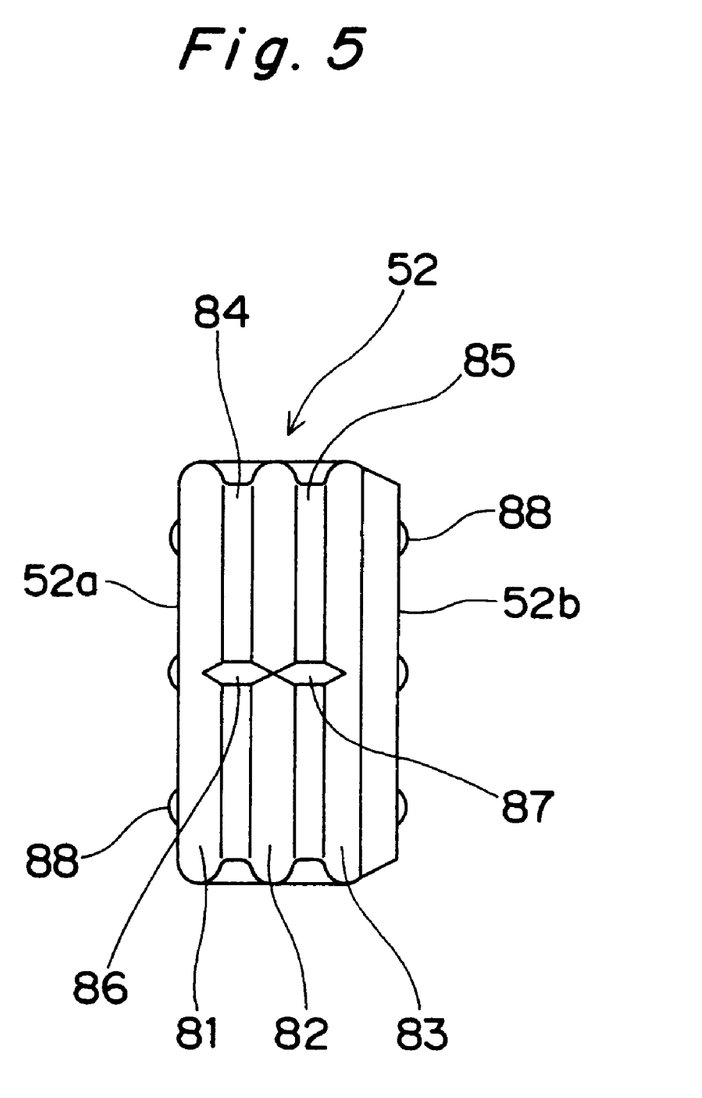
FIG. 5 is a front elevational view of a rear gasket segment employed in the gasket of FIG. 1.

FIG. 5 shows the rear gasket segment 52. The rear gasket segment 52 has a front end face 52a and a rear end face 52b each having four projections 88 in the same manner as the front gasket segment 51 and includes circumferential ribs 81, 82 and 83 which are arranged sequentially from the front end face 52a towards the rear end face 52b. The rear gasket segment 52 further has an annular recess 84 formed between the circumferential ribs 81 and 82 and an annular recess 85 formed between the circumferential ribs 82 and 83. Meanwhile, in the same manner as the front gasket segment 51, an axial rib 86 is provided at each of four circumferential positions of the annular recess 84 and an axial rib 87 is provided at each of four circumferential positions of the annular recess 85. At the time of communication between the front and rear compartments 6 and 7, the axial ribs 86 and 87 intercept the pharmaceutical liquid L flowing in the annular recesses 84 and 85 so as to prevent the pharmaceutical liquid L from flowing through the annular recesses 84 and 85.

At the time of communication between the front and rear compartments 6 and 7 by way of the bypass 1a, the gasket 50 is advanced by a plunger rod (not shown) until the front end face 51a of the front gasket segment 51 reaches the marked line 1b of FIG. 1. At this time, as shown in FIG. 2, a gap is defined between a rear end portion of the rear gasket segment 52 and a rear end portion of the bypass 1a, while a front end portion of the front gasket segment 51 is disposed forwardly of a front end portion of the bypass 1a such that the tubular body 1 at a front end side of the bypass 1a is closed by the front end portion of the front gasket segment 51.

Thus, the pharmaceutical liquid L fed under pressure into the gap between the bypass 1a and the gasket 50 as shown by the arrow b in FIG. 2 is initially introduced into the annular recesses 84 and 85 of the rear gasket segment 52 and the annular recesses 60 to 62 of the front gasket segment 51 but is intercepted by the axial ribs 86 and 87 of the rear gasket segment 52 and the axial ribs 63 to 65 of the front gasket segment 51 so as to be delivered forwardly. Then, as shown by the arrow c, the pharmaceutical liquid L is carried into the powdery medicament P along a U-shaped outflow path proceeding from the annular recess 60 to the axial slots 70 through the axial slots 71 and the annular recess 59. This outflow path of the pharmaceutical liquid L is not restricted to the U-shaped configuration but may have an arbitrary bent shape, for example, a V-shaped configuration or an S-shaped configuration.

Meanwhile, in the above described embodiment, the gasket 50 is applied to the bypass type prefilled syringe of a construction having an injection needle mounted on the front end portion of the tubular body 1 but is not restricted to the bypass type prefilled syringe of this construction. The gasket 50 may also be applied to a bypass type prefilled syringe of other constructions, e.g., a construction in which a distal end cap is mounted on a distal end of the tubular body 1 as shown in FIG. 8.

Furthermore, in the above described embodiment, the powdery medicament P and the pharmaceutical liquid L are, respectively, preliminarily stored in the front and rear compartments 6 and 7. However, in the two components stored in the front and rear compartments 6 and 7, respectively, at least the component stored in the rear compartment 7 should be liquid and thus, the two components may be liquid. Meanwhile, in case only one of the two components is liquid, it is desirable that the other component is of simply dissoluble or dispersible dosage forms such as powder and solid medicine obtained by freeze-drying. The dosage forms include sustained release drug.

For example, microsphere or the like may be recited as the sustained release drug. The microsphere includes microcapsule, microparticle, etc. More specifically, the microspheres or the microcapsules described in Japanese Patent Laid-Open Publication Nos. 60-100516 (1985), 62-201816 (1987), 02-124814 (1990), 04-321622 (1992), 05-112468 (1993), 05-194200 (1993), 06-293636 (1994), 06-145046 (1994), 06-192068 (1994), 08-169818 (1996), 09-132524 (1997), 09-221417 (1997) and 09-221418 (1997) are employed.

As injections composed of the above two components, which can be administered by the two-compartment type prefilled syringe, i.e., biologically active substances, it is possible to specify, for example, biologically active peptide, antineoplastic agent, antibiotic, antipyretic, analgesic, antiphologistic, antitussive expectorant, sedative, muscle relaxant, antiepileptic, antiulcer agent, antidepressant, antiallergic agent, cardiotonic, antiarrhythmic drug, vasodilator, hypotensive diuretic, diabetic drug, antilipemic agent, anticoagulant, hemostatic, antituberculosis drug, hormone drug, narcotic antagonist, bone resorption inhibitor, osteoplasty accelerator, angiogenesis inhibitor, etc. However, it is needless to say that the injections are not restricted to these substances.

Biologically active peptides are desirable as the biologically active substances. For example, biologically active peptide having a molecular weight of about 300 to 40,000, desirably about 400 to 30,000 and more desirably about 500 to 20,000 may be employed. Such biologically active peptide desirably has a basic group capable of forming a salt with, for example, weak acid having a pKa of not less than 4.0 including carbonic acid, acidic bicarbonate, boric acid and lower alkane monocarboxylic acid having 1 to 3 carbon atoms. Meanwhile, in place of the basic group, the biologically active peptide may also have a free acidic group or an acidic group forming a salt.

Hormonal action can be recited as a typical activity of the biologically active peptides. Meanwhile, the biologically active peptides may be any one of a natural product, a synthetic, a semisynthetic product and a product of genetic engineering, or an analogue and/or a derivative thereof. Action of these biologically active peptides may be either agonistic or antagonistic.

The biologically active peptides may include luteinizing hormone releasing agent (LH-RH) referred also to as "gonadotropin releasing agent (Gn-RH)", insulin, somatostatin, somatostatin derivative such as Sandostatin in U.S. Pat. Nos. 4,087,390, 4,093,574, 4,100,117 and 4,253,998, growth hormone (GH) in Japanese Patent Laid-Open Publication Nos. 7-1018778 (1995) and 10-265404 (1998), growth hormone releasing hormone (GH-RH), prolactin, erythropoietin (EPO), adrenocorticotropic hormone (ACTH), ACTH derivative such as ebiratide, melanocyte-stimulating hormone (MSH), thyrotropin releasing hormone ((pyr)Glu-His-ProNh2; TRH), a salt and a derivative thereof in Japanese Patent Laid-Open Publication Nos. 50-121273 (1975) and 52-116465 (1977), thyroid stimulating hormone (TSH), luteinizing hormone (LH), follicle stimulating hormone (FSH), vasopressin, vasopressin derivative such as desmopressin, oxytocin, calcitonin, glucagon, gastrin, secretin, pancreozymin, cholecystokinin, angiotensin, human placental lactogen, human chorionic gonadotropin (HCG), enkephalin, enkephalin derivative in U.S. Pat. No. 4,277,394 and EP-31567-A, endorphin, kyotorphin, interferons such as interferon-α, interferon-β and interferon-γ, interleukins such as interleukins 1 to 12, taftsin, thymopoietin, thymosin, thymostimulin, thymic humoral factor (THF), serum thymic factor (FTS) and its derivative in U.S. Pat. No. 4,229,438, tumor necrosis factor (TNF), colony stimulating factor (CSF, GCSF, GMCSF and MCSF), motilin, dinorphin, bombesin, neurotensin, cerulein, bradykinin, atrial natriuretic factor, nerve growth factor (NGF), cell growth factors such as EGF, TGF-β, PDGF, acidic FGF and basic FGF, neurotrophic factors such as NT-3, NT4, CNTF, GDNF and BDNF, peptide having endothelin antagonism and its analogue (derivative) in EP-436189-A, EP-457195-A, EP-496452-A and Japanese Patent Laid-Open Publication Nos. 3-94692 (1991) and 3-130299 (1991), insulin receptor, insulin-like growth factor (IGF)-1 receptor, IGF-2 receptor, transferrin receptor, epidermal growth factor, low density lipoprotein (LDL) receptor, macrophage scavenger receptor, GLUT-4 transporter, growth hormone receptor, peptide derived from α1 domain of major histocompatibility class I antigen complex (MHC-I) having activity for hampering endogeny of leptin receptor ("Proceedings of the National Academy of Sciences of the United States of America", Vol. 91, p.p. 9086–9090 (1994) and Vol. 94, p.p. 11692–11697 (1997)) and its analogue (derivative), and a fragment or a fragment derivative thereof.

In case the biologically active peptide is a salt, a pharmacologically acceptable salt or the like may be used. For example, in case the biologically active peptide has a basic group such as an amino group in its molecule, salts formed by the basic group and inorganic acids such as hydrochloric acid, sulfuric acid, nitric acid and boric acid or organic acids such as carbonic acid, acidic bicarbonate, succinic acid, acetic acid, propionic acid and trifluoroacetic acid may be used. Meanwhile, in case the biologically active peptide has an acidic group such as a carboxyl group in its molecule, salts formed by the acidic group and inorganic bases including alkaline metals such as sodium and potassium and alkaline earth metals such as calcium and magnesium or organic bases including organic amines such as triethylamine and basic amino acids such as arginine may be used. Furthermore, the biologically active peptide may form metal complex compounds such as a copper complex and a zinc complex.

As concrete examples of the biologically active peptides desirable for use, it is possible to recite an LH-RH analogue and its salt effective for contraception and diseases dependent on either LH-RH of prostatic cancer, prostatic hypertrophy, endometriosis, myoma of the uterus, fibroma of the uterus, precocious puberty and breast cancer or a hormone derived from the LH-RH as well as a somatostatin derivative and its salt effective for diseases dependent on growth hormone and a hormone derived from the growth hormone and diseases of the digestive system such as peptic ulcer.

Concrete examples of the LH-RH analogue and its salt may include peptides described in "Treatment with GnRH analogs: Controversies and perspectives" published in 1966 by The Parthenon Publishing Group Ltd., Japanese Patent National Publication No. 3-503165 (1991) and Japanese Patent Laid-Open Publication Nos. 3-101695 (1991), 7-97334 (1995) and 8-259460 (1996).

As a concrete example of a biologically active peptide having LH-RH antagonism, i.e., an LH-RH antagonist, a biologically active peptide expressed by the following general formula [Ia] or its salt may be recited.

X-D2Nal-D4ClPhe-D3Pal-Ser-A-B-Leu-C-Pro-DAlaNH$_2$ [Ia]

In the formula, "X" denotes N(4H$_2$-furoyl)Gly or NAc, "A" denotes a residual group selected from NMeTyr, Tyr, Aph(Atz) and NMeAph(Atz), "B" denotes a residual group selected from DLys(Nic), DCit, DLys(AzaglyNic), DLys (AzaglyFur), DhArg(Et$_2$), DAph(Atz) and DhCi and "C" denotes Lys(Nisp), Arg or hArg(Et$_2$).

More specifically, the biologically active peptide having LH-RH antagonism, i.e., LH-RH antagonist may be NAcD2Nal-D4ClPhe-D3Pal-Ser -NMeTyr-DLys(Nic)-Leu-Lys(Nisp)-Pro-DAlaNH$_2$, N(4H$_2$-furoyl)Gly-D2Nal-D4ClPhe-D3Pal-Ser-NMeTyr-DLys(Nic)-Leu-Lys(Nisp)-Pro-DAlaNH$_2$, cetrorelix, ganirelix, antarelix, detirelix, azaline, antide, ramorelix and abarelix. These peptides can be produced by the methods described in the above prior art documents or similar methods.

As a concrete example of a biologically active peptide having LH-RH agonistic action, i.e., an LH-RH agonist, a biologically active peptide expressed by the following general formula [Ib] or its salt may be recited.

5-oxo-Pro-His-Trp-Ser-Tyr-Y-Leu-Arg-Pro-Z [Ib]

In the formula, "Y" denotes a residual group selected from DLeu, DAla, DTrp, DSer(tBu), D2Nal and DHis (ImBzl) and "Z" denotes NH—C$_2$H$_5$ or Gly-NH$_2$. Especially, a peptide in which "Y" is Dleu and "Z" is NH—C$_2$H$_5$ or its salt is suitable. These peptides can be produced by the methods described in the above prior art documents or similar methods.

A concrete example of the somatostatin derivative or its salt is described in, for example, "Proceedings of the National Academy of Sciences of the United States of America", Vol. 93, p.p. 12513–12518 (1996) or the documents cited therein.

Furthermore, as a concrete example of a somatostatin derivative selectively effective for tumor in somatostatin analogues, a biologically active peptide described in U.S. Pat. No. 5,480,870 or EP-505680-A and having the following formula may be recited.

Meanwhile, Sandostatin in U.S. Pat. Nos. 4,087,390, 4,093,574, 4,100,117 and 4,253,998 may be suitable.

In the above described biologically active peptides, 5-oxo-Pro-His-Trp-Ser-Tyr-DLeu-Leu-Arg-Pro-NH—C$_2$H$_5$ (leuprorelin) or its salt, especially, acetate is preferable.

As the above biologically active substances, non-peptide drugs, etc. may be used. More specifically, compounds described in, for example, Japanese Patent No. 2946298 and Japanese Patent Laid-Open Publication Nos. 3-232880 (1991) and 4-364179 (1992) may be recited as the drugs.

As is clear from the foregoing description of the gasket 50 for the bypass type prefilled syringe, according to the present invention, at the time of communication between the front and rear compartments 6 and 7 via the bypass 1a, since the tubular body 1 at the front end side of the bypass 1a is closed by the front end portion of the front gasket segment 51 and the pharmaceutical liquid L is introduced into the powdery medicament P along the U-shaped outflow path proceeding from the annular recess 60 to the axial slots 70 by way of the axial slots 71 and the annular recess 59, a squirt phenomenon of the pharmaceutical liquid L is prevented positively. As a result, since the powdery medicament P is sufficiently dissolved or dispersed in the pharmaceutical liquid L, satisfactory injection liquid can be prepared at all times.

Meanwhile, in the gasket 50 for the bypass type prefilled syringe, according to the present invention, at the time of communication between the front and rear compartments 6 and 7 via the bypass 1a, since the pharmaceutical liquid L carried into the annular recesses 84 and 85 of the rear gasket segment 52 and the annular recesses 60 to 62 of the front gasket segment 51 is intercepted by the axial ribs 86 and 87 and the axial ribs 63 to 65, respectively so as to be delivered forwardly, the pharmaceutical liquid L is efficiently introduced into the powdery medicament P without incurring such a loss that the pharmaceutical liquid L remains in the annular recesses 84 and 85 of the rear gasket segment 52 and the annular recesses 60 to 62 of the front gasket segment 51 for a long time.

Furthermore, in the gasket 50 for the bypass type prefilled syringe, according to the present invention, since the cross-sectional area of the flow path of the axial slot 70 opening to the front end face 51a of the front gasket segment 51 is set to be larger than that of the axial slot 71 formed on the circumferential rib 55, delivery speed of the pharmaceutical liquid L in the axial slots 70 drops below that of the pharmaceutical liquid L in the axial slots 71 in the U-shaped outflow path at the time of communication between the front and rear compartments 6 and 7 via the bypass 1a, so that the squirt phenomenon of the pharmaceutical liquid is prevented more positively.

In addition, in the gasket for the bypass type prefilled syringe, according to the present invention, since the outside diameter D1 of the circumferential ribs 54 and 55 is set to be equal to or larger than the inside diameter of the tubular body 1 but smaller than the outside diameter D2 of the circumferential ribs 56 to 58, the small-diameter circumferential ribs 54 and 55 are lightly fitted into the tubular body 1 forwardly of the bypass 1a at the time of communication between the front and rear compartments 6 and 7 via the bypass 1a, so that an operation of advancing the front end of the gasket 50 to the marked line 1b can be performed smoothly.

What is claimed is:

1. A gasket for dividing interior space of a tubular body of a bypass type prefilled syringe into front and rear compartments for preliminarily storing medicament and pharmaceutical liquid, respectively, with the tubular body being formed with a bypass for establishing communication between the front and rear compartments, the gasket comprising:

a plurality of circumferential ribs which include at least first, second and third circumferential ribs disposed sequentially further away from the front compartment;

a plurality of annular recesses each of which is formed between neighboring ones of the circumferential ribs and which include at least a first annular recess formed between the first and second circumferential ribs and a second annular recess formed between the second and third circumferential ribs;

a first axial slot which extends through the first circumferential rib and the first annular recess;

a second axial slot which is formed at a circumferential position of the second circumferential rib deviating from the first axial slot so as to bring the first and second annular recesses into communication with each other; and an axial rib which is formed on each of other ones of the annular recesses than the first annular recess;

wherein at the time of communication between the front and rear compartments via the bypass, a bent outflow path for delivering the pharmaceutical liquid into the front compartment in a state where the tubular body at a front end side of the bypass is closed by a front end portion of the gasket is sequentially formed by the second annular recess, the second axial slot, the first annular recess and the first axial slot.

2. A gasket as claimed in claim 1, wherein a cross-sectional area of a flow path of the first axial slot is set to be larger than that of the second axial slot.

3. A gasket as claimed in claim 2, wherein an outside diameter of the first and second circumferential ribs is set to be larger than an inside diameter of the tubular body but smaller than an outside diameter of other ones of the circumferential ribs.

4. A gasket as claimed in claim 1, wherein an outside diameter of the first and second circumferential ribs is set to be larger than an inside diameter of the tubular body but smaller than an outside diameter of other ones of the circumferential ribs.

5. A gasket for dividing interior space of a tubular body of a bypass type prefilled syringe into front and rear compartments for preliminarily storing medicament and pharmaceutical liquid, respectively, with the tubular body being formed with a bypass for establishing communication between the front and rear compartments, the gasket comprising:

a plurality of circumferential ribs which include at least first, second and third circumferential ribs disposed sequentially further away from the front compartment;

a plurality of annular recesses each of which is formed between neighboring ones of the circumferential ribs and which include at least a first annular recess formed between the first and second circumferential ribs and a second annular recess formed between the second and third circumferential ribs;

a first axial slot which extends through the first circumferential rib and the first annular recess; and a second axial slot which is formed at a circumferential position of the second circumferential rib deviating from the first axial slot so as to bring the first and second annular recesses into communication with each other;

wherein at the time of communication between the front and rear compartments via the bypass, a bent outflow path for delivering the pharmaceutical liquid into the front compartment in a state where the tubular body at a front end side of the bypass is closed by a front end portion of the gasket is sequentially formed by the second annular recess, the second axial slot, the first annular recess and the first axial slot; and wherein a cross-sectional area of a flow path of the first axial slot is set to be larger than that of the second axial slot.

6. A gasket as claimed in claim 5, wherein an outside diameter of the first and second circumferential ribs is set to be larger than an inside diameter of the tubular body but smaller than an outside diameter of other ones of the circumferential ribs.

7. A gasket for dividing interior space of a tubular body of a bypass type prefilled syringe into front and rear compartments for preliminarily storing medicament and pharmaceutical liquid, respectively, with the tubular body being formed with a bypass for establishing communication between the front and rear compartments, the gasket comprising:

a plurality of circumferential ribs which include at least first, second and third circumferential ribs disposed sequentially further away from the front compartment;

a plurality of annular recesses each of which is formed between neighboring ones of the circumferential ribs and which include at least a first annular recess formed between the first and second circumferential ribs and a second annular recess formed between the second and third circumferential ribs;

a first axial slot which extends through the first circumferential rib and the first annular recess; and a second axial slot which is formed at a circumferential position of the second circumferential rib deviating from the first axial slot so as to bring the first and second annular recesses into communication with each other;

wherein at the time of communication between the front and rear compartments via the bypass, a bent outflow path for delivering the pharmaceutical liquid into the front compartment in a state where the tubular body at a front end side of the bypass is closed by a front end portion of the gasket is sequentially formed by the second annular recess, the second axial slot, the first annular recess and the first axial slot; and wherein an outside diameter of the first and second circumferential ribs is set to be larger than an inside diameter of the tubular body but smaller than an outside diameter of other ones of the circumferential ribs.

8. A gasket for dividing interior space of a tubular body of a bypass type prefilled syringe into front and rear compartments for preliminarily storing medicament and pharmaceutical liquid, respectively, with the tubular body being formed with a bypass for establishing communication between the front and rear compartments, the gasket comprising:

a plurality of circumferential ribs which include at least first, second and third circumferential ribs disposed sequentially further away from the front compartment;

a plurality of annular recesses each of which is formed between neighboring ones of the circumferential ribs and which include at least a first annular recess formed between the first and second circumferential ribs and a second annular recess formed between the second and third circumferential ribs;

a first axial slot which extends through the first circumferential rib and the first annular recess; and a second axial slot which is formed at a circumferential position of the second circumferential rib deviating from the first axial slot so as to bring the first and second annular recesses into communication with each other;

wherein at the time of communication between the front and rear compartments via the bypass, a bent outflow path for delivering the pharmaceutical liquid into the front compartment in a state where the tubular body at a front end side of the bypass is closed by a front end portion of the gasket is sequentially formed by the second annular recess, the second axial slot, the first annular recess and the first axial slot; and wherein said gasket is constituted by a front gasket segment formed with at least the bent outflow path of the pharmaceutical liquid and a rear gasket segment abutting on the front gasket segment.

* * * * *